United States Patent
Lutz

(10) Patent No.: US 8,105,823 B2
(45) Date of Patent: Jan. 31, 2012

(54) BIOGAS INSTALLATION FOR PRODUCTION OF BIOGAS FROM BIOMASS, AND METHODS FOR OPERATION OF THE BIOGAS INSTALLATION

(75) Inventor: Peter Lutz, München (DE)

(73) Assignee: Bekon Energy Technologies GmbH & Co., KG, Unterfohring (DE)

( * ) Notice: Subject to any disclaimer, the term of this patent is extended or adjusted under 35 U.S.C. 154(b) by 0 days.

(21) Appl. No.: 12/859,093

(22) Filed: Aug. 18, 2010

(65) Prior Publication Data

US 2010/0311141 A1    Dec. 9, 2010

Related U.S. Application Data

(62) Division of application No. 12/126,708, filed on May 23, 2008.

(30) Foreign Application Priority Data

May 29, 2007 (DE) .................. 10 2007 024 911

(51) Int. Cl.
*C12M 1/107* (2006.01)
*C12M 1/00* (2006.01)
*C12M 3/00* (2006.01)
*G01N 1/22* (2006.01)

(52) U.S. Cl. ............... 435/300.1; 435/289.1; 435/294.1; 73/863; 73/864

(58) Field of Classification Search ............... 435/300.1, 435/289.1, 294.1; 73/863–864
See application file for complete search history.

(56) References Cited

U.S. PATENT DOCUMENTS

| 6,969,562 B2 | 11/2005 | Su et al. |
| 7,481,940 B2 | 1/2009 | Clifford, III et al. |
| 2006/0111575 A1* | 5/2006 | DeCourcy et al. ............ 549/248 |
| 2006/0223154 A1 | 10/2006 | Kohr |
| 2008/0299634 A1 | 12/2008 | Lutz |
| 2009/0239209 A1 | 9/2009 | Lutz |

FOREIGN PATENT DOCUMENTS

| DE | 34 38 057 A1 | 4/1986 |
| DE | 197 19 323 A1 | 11/1998 |

(Continued)

OTHER PUBLICATIONS

English translation of Lutz (WO 02/06439).*

(Continued)

*Primary Examiner* — Nathan Bowers
*Assistant Examiner* — Gautam Prakash
(74) *Attorney, Agent, or Firm* — Morrison & Foerster LLP

(57) ABSTRACT

A biogas installation for production of biogas from biomass and methods for starting and shutting down a fermenter are disclosed. When biomass in a fermenter is used up, biogas production must stop, the fermented biomass removed, and the fermenter filled with fresh biomass. Biogas production and utilization is maintained for as long as possible. When the methane concentration in the biogas outlet falls below an upper limit, the biogas line is disconnected. The biogas/off-gas mixture is fed out via an exhaust chimney until the methane concentration has fallen to a lower limit. The fermenter to be shut down is purged with fresh air, and the off-gas/biogas/fresh air mixture is fed out via the exhaust chimney until the carbon-dioxide concentration in the off-gas/biogas/fresh air mixture has fallen to a first limit. The fermenter is then opened to unload the consumed biomass and load fresh biomass.

10 Claims, 15 Drawing Sheets

FOREIGN PATENT DOCUMENTS

| | | |
|---|---|---|
| DE | 20319847 U | 5/2005 |
| EP | 0934998 | 8/1999 |
| EP | 1301583 | 4/2003 |
| EP | 1354940 | 10/2003 |
| EP | 1 681 274 A2 | 7/2006 |
| EP | 1762607 | 3/2007 |
| EP | 1 997 875 A1 | 12/2008 |
| RU | 2254700 | 6/2005 |
| SU | 1748693 A1 | 7/1992 |
| WO | WO 02/06439 * | 1/2002 |
| WO | WO-0206439 | 1/2002 |

OTHER PUBLICATIONS

Eurasian Search Report mailed Jul. 1, 2009, for EA Application No. 2420-158974, two pages.

Search Report for Eurasian Patent Application No. 200801217, dated Oct. 13, 2008.

* cited by examiner

BIOGAS INSTALLATION FOR PRODUCTION OF BIOGAS FROM BIOMASS, AND METHODS FOR OPERATION OF THE BIOGAS INSTALLATION

CROSS REFERENCE TO RELATED APPLICATIONS

This is a divisional of U.S. patent application Ser. No. 12/126,708, filed on May 23, 2008, the entire disclosure of which is incorporated herein by reference.

FIELD OF THE INVENTION

The invention relates to a biogas installation for production of biogas from biomass having at least one fermenter, to a method for shutting down a fermenter, and to a method for starting a fermenter

BACKGROUND OF THE INVENTION

So-called "dry fermentation" allows pourable biomasses from agriculture, from biological waste and from communal cultivated areas to be converted to methane without having to convert the materials to a liquid substrate which can be pumped. Biomasses with a dry substance component of up to 50% can be fermented. This dry fermentation method is described, for example, in EP 0 934 998.

In the case of "dry" fermentation, the material to be fermented is not stirred into a liquid phase as is the case, for example, with liquid fermentation of bio waste. Instead of this, the fermentation substrate which has been introduced into the fermenter is kept moist all the time by taking the percolate at the bottom of the fermenter away and spraying it over the biomass again. This results in optimum living conditions for the bacteria. During the recirculation of the percolate, the temperature can also be regulated, and it is possible to add additives for process optimisation.

WO 02/06439 discloses a bioreactor or a fermenter in the form of a prefabricated garage which is operated using the principle of dry fermentation in the so-called batch process. In this case, after seeding with already fermented material, the fermenter is filled with the fermentation substrate by means of tractor shovels. The fermentation container is constructed in the form of a garage and is closed by a gastight door. The biomass is fermented with air being excluded, with no further thorough mixing during the process, and with no additional material being supplied. The percolate which seeps out of the material being fermented is drawn off via a drainage groove, is temporarily stored in a tank, and is sprayed over the fermentation substrate again, in order to moisturise it. The fermentation process takes place in the mesophilic temperature range between 34 and 37° C., with the temperature being created by means of bottom heating and wall heating.

The resultant biogas can be used to obtain electricity and heat in a cogeneration system that generates heat and electric power at the same time. In order to ensure that sufficient biogas is always available for the cogeneration system, a plurality of fermentation containers are operated with offset timings in the dry fermentation installation. At the end of the dwell time, the fermenter area is completely emptied and is then refilled. The fermented substrate is supplied to a post-composting process, resulting in an organic fertiliser that is comparable to conventional compost.

The batch operation means the individual fermenters must be shut down from time to time, that is to say the biogas production must be stopped, the fermented biomass must be removed from the respective fermenter, and the fermenter must be filled with fresh biomass, with biogas production being resumed. During this process, it is necessary for safety reasons to prevent an explosive biogas/air mixture from being created while the individual fermenters are being loaded and unloaded.

For this purpose, it is known from EP 1301583 B for a fermenter that is in use to be flooded with off-gas containing carbon dioxide from the cogeneration system that is being operated with biogas, in the event of an explosion risk, that is to say if air has entered the fermenter.

SUMMARY OF THE INVENTION

Starting out from a biogas installation according to EP 1301583 B, the object of the present invention is to make safer the process of unloading consumed biomass from the fermenter, and loading it with fresh biomass.

This object is achieved by the features of the claims.

The biogas installation according to comprises the necessary components to allow a fermenter to be shut down and unloaded safely, and likewise to be started safely.

The measures result in the biogas production and utilisation being maintained for as long as possible even during the shutdown and purging with off-gas containing carbon dioxide, that is to say the biogas/off-gas mixture of the fermenter to be shut down is still supplied to the biogas consumer until the quality of the mixture falls below a predetermined level. Only when the methane concentration in the biogas outlet falls below an upper limit value is the biogas line leading to the biogas consumer disconnected from the biogas outlet. The biogas/off-gas mixture, which now just contains a small amount of methane, is fed out via an exhaust chimney. This is done until the methane concentration has fallen to a lower limit value, where the biogas/off-gas mixture now contains virtually no methane. After this, the fermenter to be shut down is purged with fresh air instead of with off-gas containing carbon dioxide, and the off-gas/biogas/fresh air mixture is fed out via the exhaust chimney until the carbon-dioxide concentration in the off-gas/biogas/fresh air mixture has fallen to a first limit value. Only then is the fermenter opened in order to unload the consumed biomass and in order to load the fermenter with fresh biomass again. The previous purging processes with off-gas and fresh air allow the fermenter to be opened, unloaded and loaded, without any risk to the operator.

According to one preferred refinement of the invention, when the methane concentration reaches the upper limit value, the biogas/off-gas mixture is not emitted to the environment via the exhaust chimney but is passed to an off-gas flare where it is burnt off. If required, the off-gas flare can be supplied with additional fuel so that combustion always takes place. The biogas/off-gas mixture is burnt off until the methane concentration in the biogas/off-gas mixture falls below a medium limit value, which is between the upper and the lower limit value.

According to one preferred refinement of the invention, while the biofermenter that has been shut down is being unloaded and loaded through the open loading and unloading opening, fresh air is sucked in and the gas mixture that is sucked in is passed to the exhaust chimney via the purging gas inlet or via the biogas outlet. Alternatively, a specific fresh-air extraction connection can also be provided in the fermenter.

The advantageous refinement of the invention ensures that fresh air is sucked in continuously while the fermenter is being unloaded and loaded.

The method according to the invention for (re)starting the fermenter which has been shut down safely prevents an explosive biogas/air mixture being formed during starting.

This fermenter which has been started again is connected to the biogas line at a fourth methane concentration limit value, which is the same as the upper limit value The off-gas for purging the fermenter to be shut down is provided, for example, by an internal combustion engine.

According to one preferred embodiment of the invention, the off-gas which contains carbon dioxide is provided by a biogas processing device connected downstream from the at least one fermenter.

The other dependent claims relate to advantageous refinements of the invention.

BRIEF DESCRIPTION OF THE DRAWINGS

Further details, features and advantages of the invention will become evident from the following description of exemplary embodiments with reference to the drawings, in which.

DETAILED DESCRIPTION OF THE PREFERRED EMBODIMENTS

Figure 1:
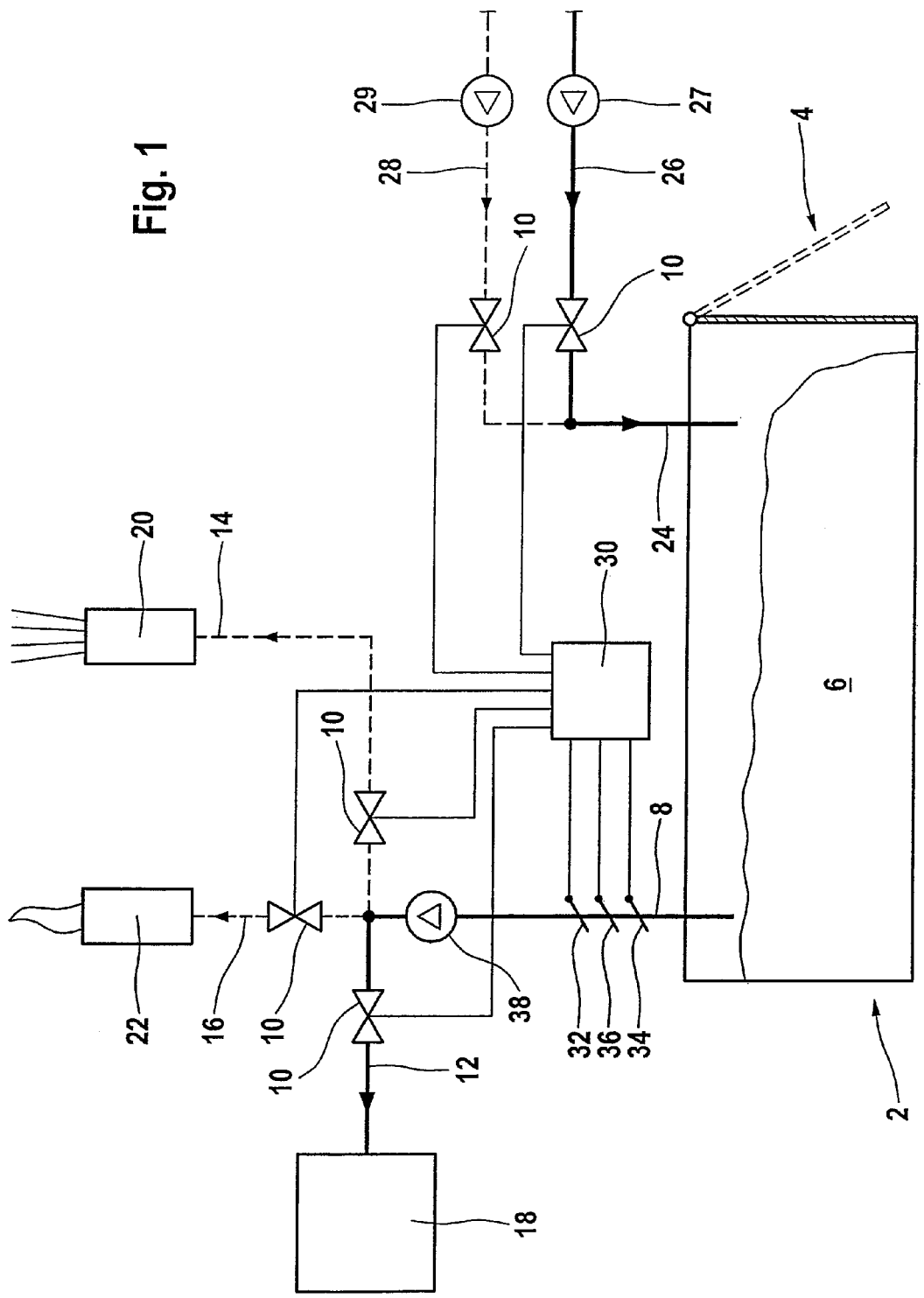
FIGS. 1 to 7 show schematic illustrations of various operating states during the shut down process and during (re) starting of a fermenter.

FIGS. 1 to 7 show a first embodiment of a biogas installation according to the present invention with a single fermenter 2. The fermenter 2 has a cuboid shape and is constructed approximately in the form of a prefabricated garage. The fermenter 2 can be filled with biomass 6, and can be emptied again by means of a tractor shovel through a loading and unloading opening 4 which extends over one of the end faces of the cuboid fermenter 2. Reference is made to WO 02/06439 with regard to details of the construction of the fermenter 2.

The fermenter 2 also has a biogas outlet 8, which can be connected via valves 10 to a biogas line 12, a first biogas/off-gas line 14 and a second biogas/off-gas line 16. The biogas line 12 leads to a cogeneration system 18 as a biogas utilisation device. The first biogas/off-gas line 14 leads to a bio off-gas chimney 20. The second biogas/off-gas line 16 leads to an off-gas flare 22. Furthermore, the fermenter 2 has a purging gas inlet 24, which can be connected via valves 10 to an off-gas line 26 or to a fresh air line 28. An off-gas fan 27 is arranged in the off-gas line 26, and can be used to pump off-gas into the fermenter 2. A fresh air fan 29 is arranged in the fresh air line 28 in order to suck fresh air in from the environment. Off-gas containing carbon dioxide is passed via the off-gas line 26 as purging gas into the fermenter 2, and fresh air is passed into the fermenter 2 via the fresh air line 28.

The valves 10 are connected to a control device 30, and are opened or closed by the control device 30. The control device 30 is also connected to a first measurement sensor 32, which is arranged in the biogas outlet 8 and detects the methane concentration in the respective gas mixture. The control device 30 is also connected to a second measurement sensor 34, which is likewise arranged in the biogas outlet 8 and detects the carbon-dioxide concentration in the respective gas mixture. The control device 30 is also connected to a third measurement sensor 36, which is arranged in the biogas outlet 8 and detects the gas volume flow in the biogas outlet. If required, the extraction of gas from the fermenter 2 can be assisted by a fan 38 which is arranged in the biogas outlet.

FIGS. 1 to 7 show various phases of the shut down process and process of starting the fermenter 2, with active lines and positions of components being illustrated by solid lines, while lines and positions of components which are inactive or are shut down are illustrated by dashed lines.

FIG. 1 shows the first phase of shutting down the fermenter 2, in which off-gas containing carbon dioxide is pumped via the off-gas line 26 and the purging gas inlet 24 into the interior of the fermenter 2. The biogas outlet 8 is connected, as before, to the biogas line 12, so that the biogas/off-gas mixture is passed on to the cogeneration system 18.

Figure 2:
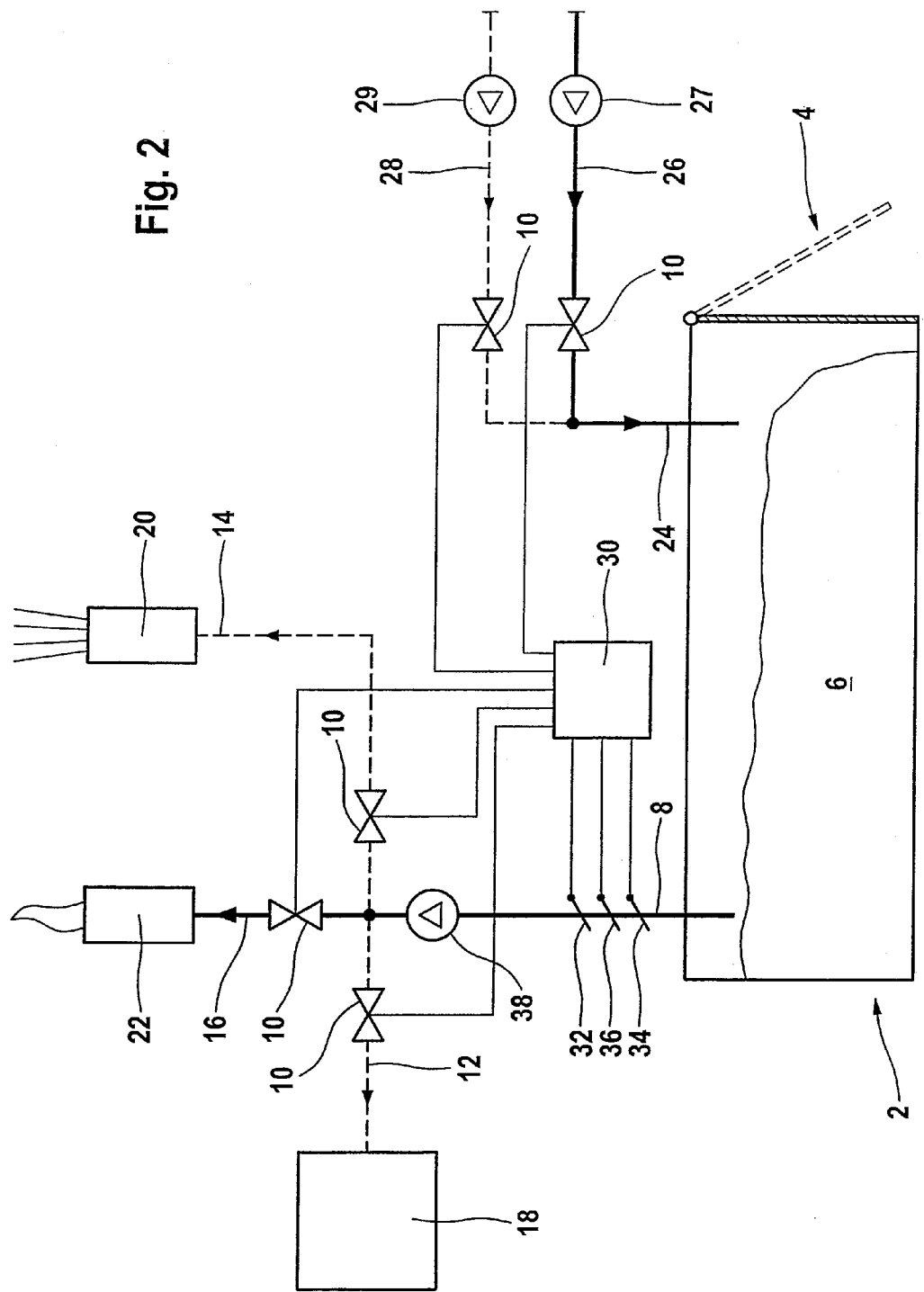

Only when the methane concentration detected by the first measurement sensor 32 in the biogas outlet 8 has fallen below an upper limit value is the valve 10 in the biogas line 12 closed by the control device 30, and the valve 10 in the second biogas/off-gas line 16 is opened, as is illustrated in FIG. 2. In this second phase of shutting down the fermenter 2, the biogas/off-gas mixture is burnt in the off-gas flare 22. If required, this combustion process can be assisted by adding additional fuel.

Figure 3:
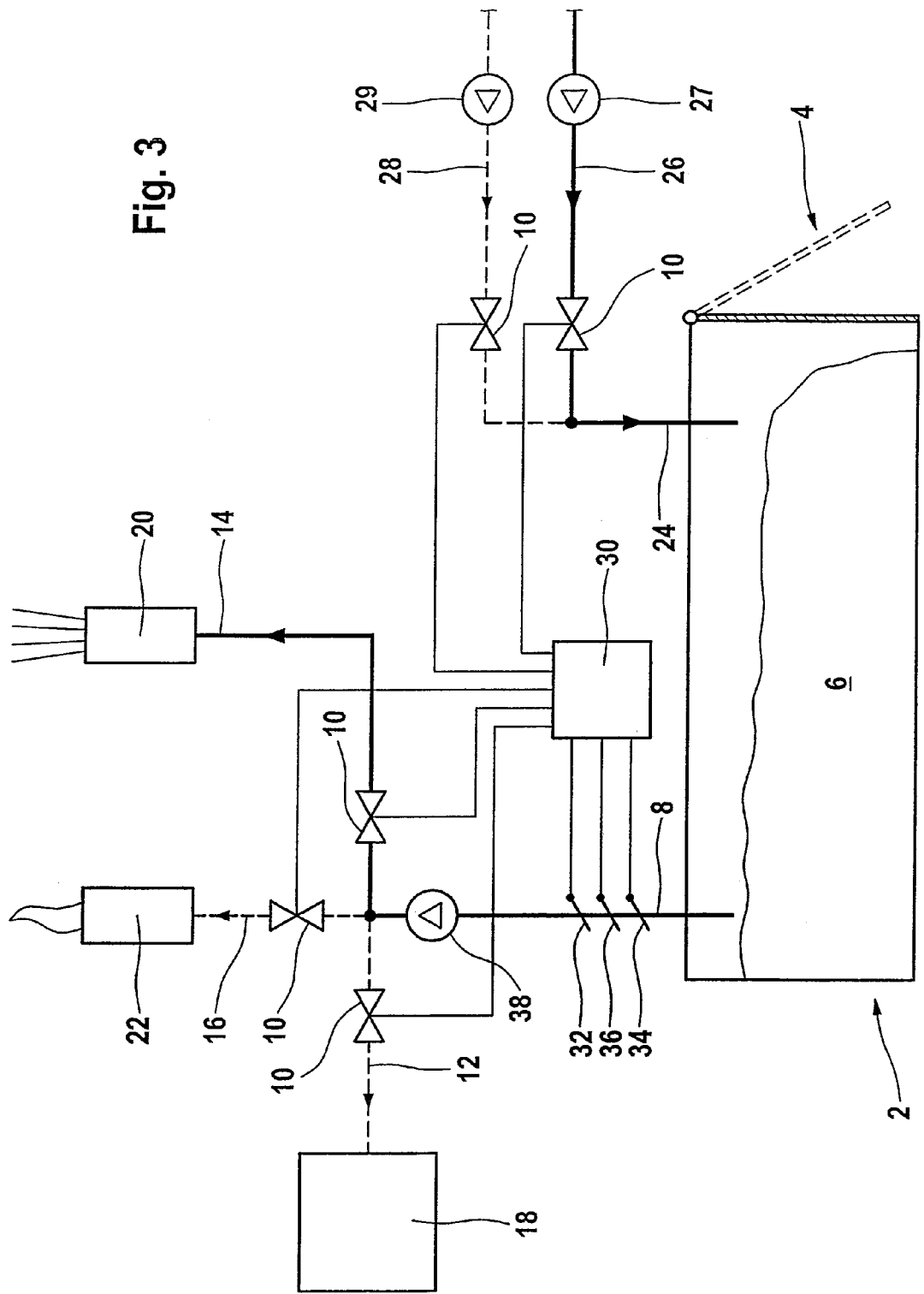

When the methane concentration detected by the first measurement sensor 32 in the biogas outlet 8 has fallen below a medium limit value, the valve 10 in the second biogas/off-gas line 16 is closed by the control device 30 and the valve 10 in the first biogas/off-gas line 14 is opened, as is illustrated in FIG. 3. In this third phase of shutting down the fermenter 2, the biogas/off-gas mixture is emitted to the environment via the off-gas chimney 20.

Figure 4:
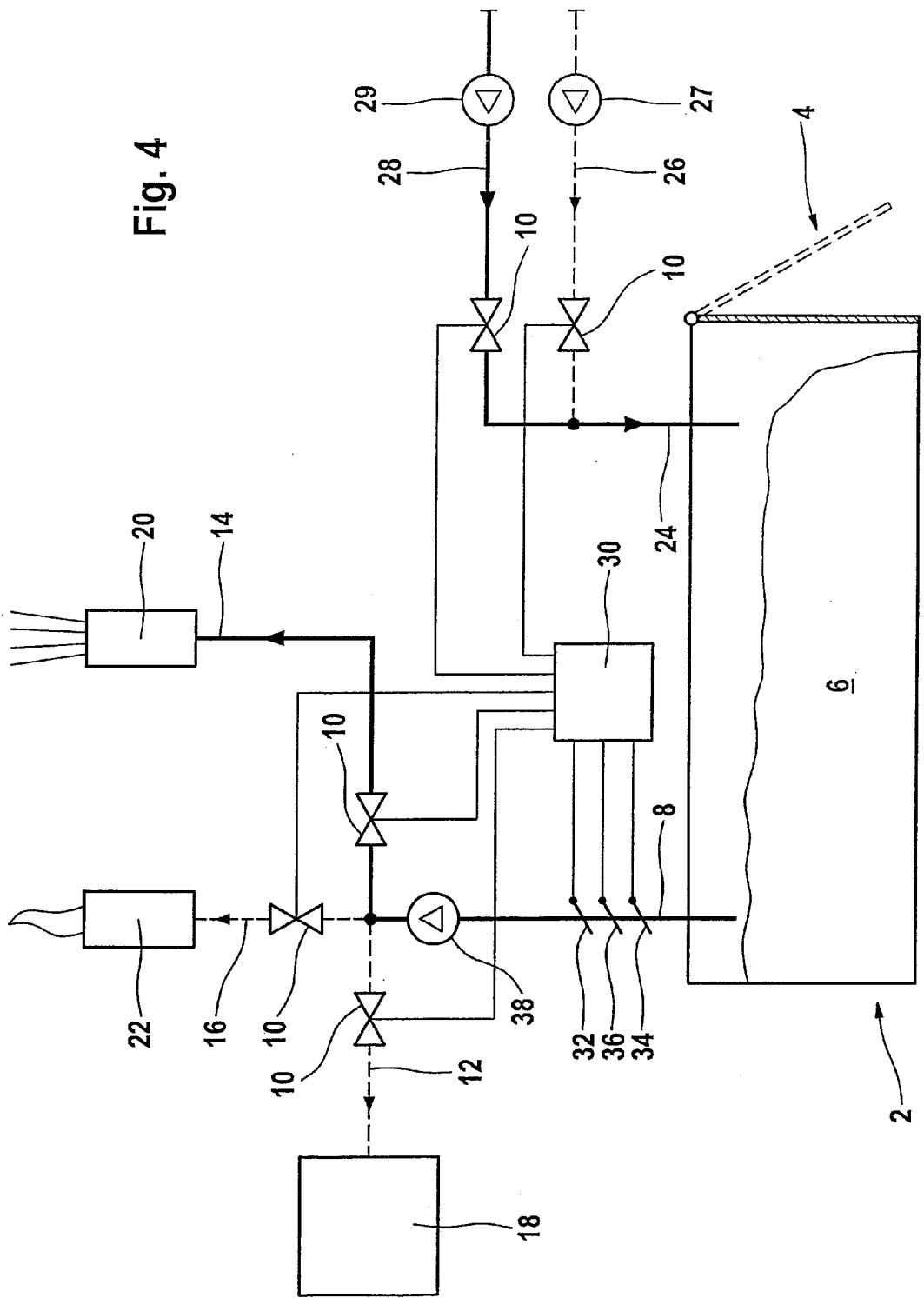

When the methane concentration detected by the first measurement sensor 32 in the biogas outlet 8 has fallen below a lower limit value, the valve 10 in the off-gas line 26 is closed by the control device 30 and the valve 10 in the fresh air line 28 is opened, as is illustrated in FIG. 4. In this fourth phase of shutting down the fermenter 2, fresh air is pumped into the fermenter 2 via the fresh air line 28 and the purging gas inlet 24. The off-gas/air mixture is emitted further to the environment via the biogas outlet 8 and the first biogas/off-gas line 14 in the off-gas chimney 20.

Figure 5:
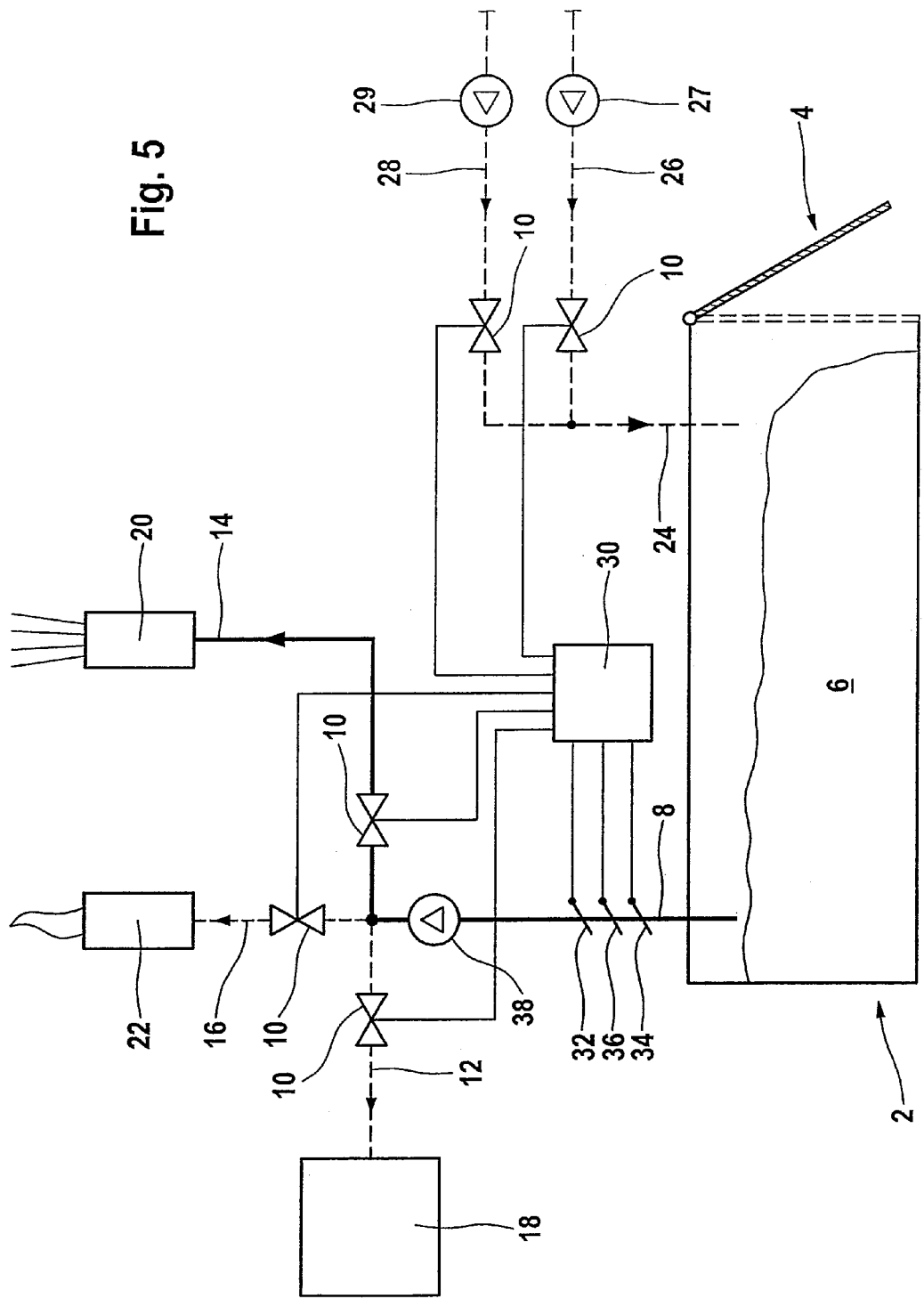

When the carbon-dioxide concentration detected by the second measurement sensor 34 in the biogas outlet 8 has fallen below a first limit value, the valve 10 in the fresh air line 28 is closed by the control device 30, and the loading and unloading opening 4 is opened, as is illustrated in FIG. 5. At the same time, the fan 38 is used to suck fresh air in via the open loading and unloading opening, and to emit it to the environment via the off-gas chimney 20. This prevents biogas residues which the fermented biomass still contains from representing a risk to the operator during the unloading process.

Figure 6:
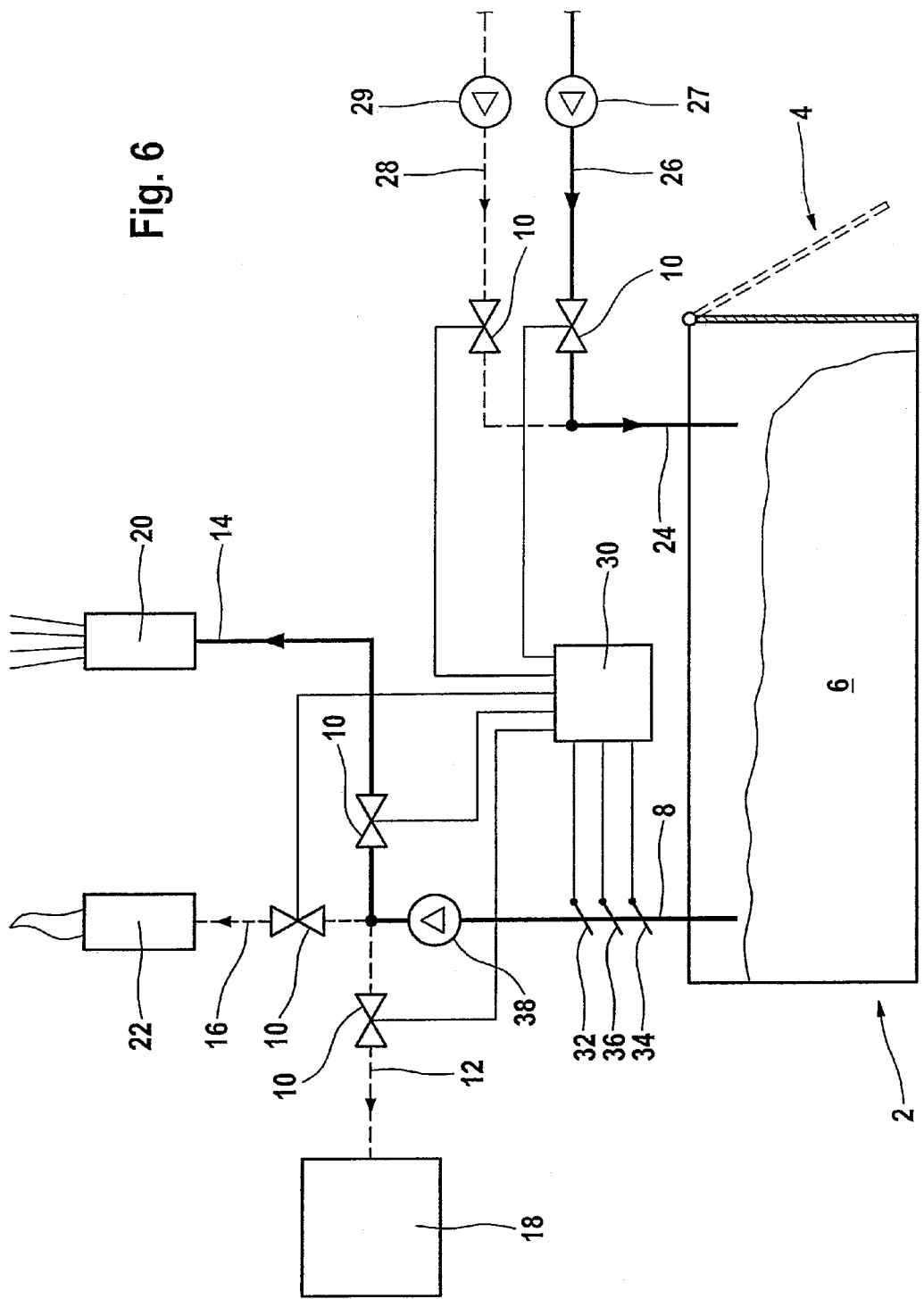

Once the fermenter 2 has been loaded with fresh biomass again, the loading and unloading opening 4 is closed, the connection between the biogas outlet 8 and the off-gas chimney 20 is maintained via the first biogas/off-gas line 14, and the control device 30 opens the valve 10 in the off-gas line 26, so that the off-gas which contains carbon dioxide is pumped into the fermenter 2, see FIG. 6. This is continued until the carbon-dioxide concentration detected by the second measurement sensor 34 in the biogas outlet 8 reaches or exceeds a second limit value.

Figure 7:
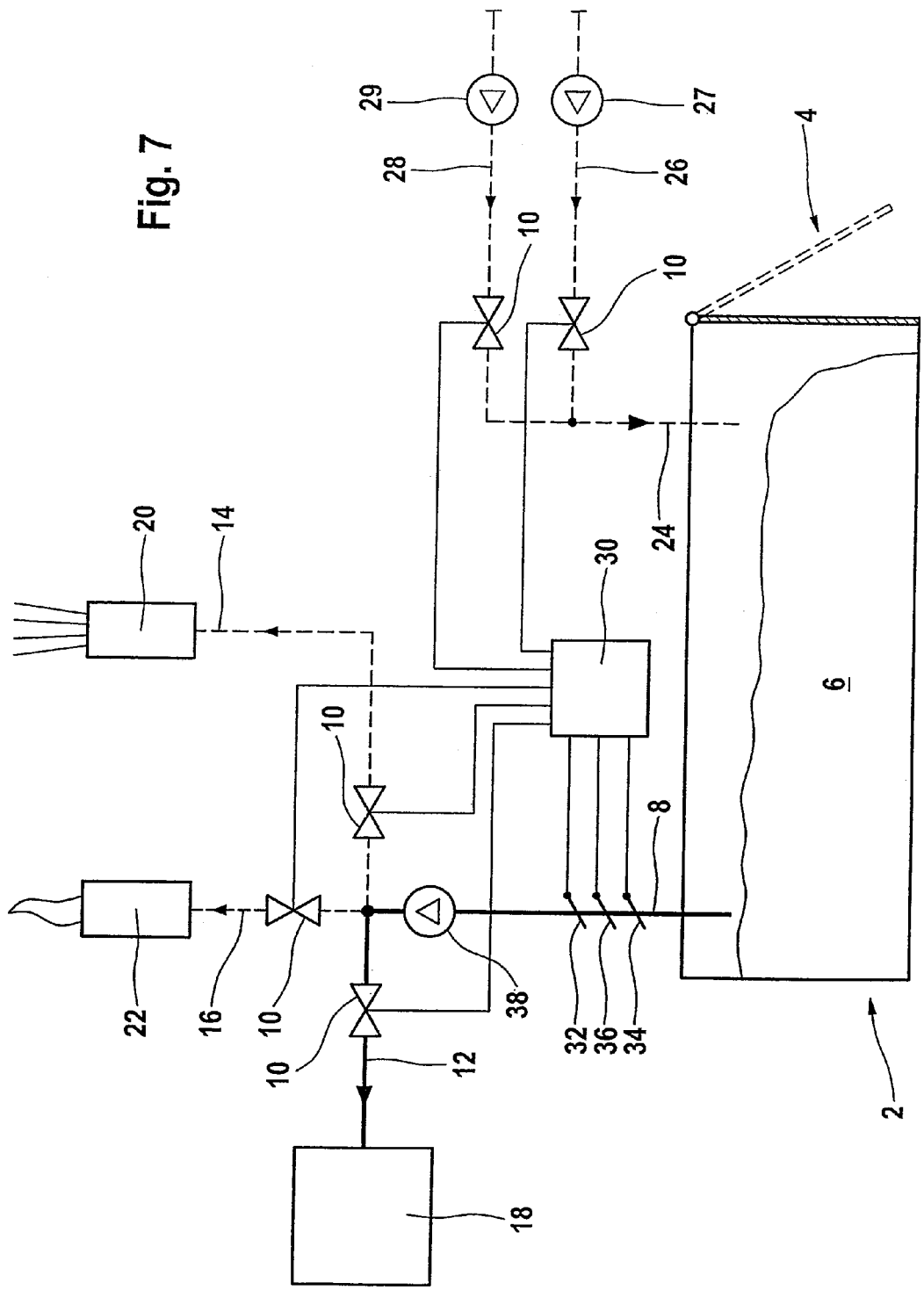

When the carbon-dioxide concentration has reached this second limit value, the control device 30 closes the valve 10 in the off-gas line 26 and in the first biogas/off-gas line 14, and opens the valve 10 in the biogas line 12, as is illustrated in FIG. 7. The biogas production phase has therefore been reached again, and the biogas produced in the fermenter 2 is supplied via the biogas line 12 to the cogeneration system 18.

Figure 8:
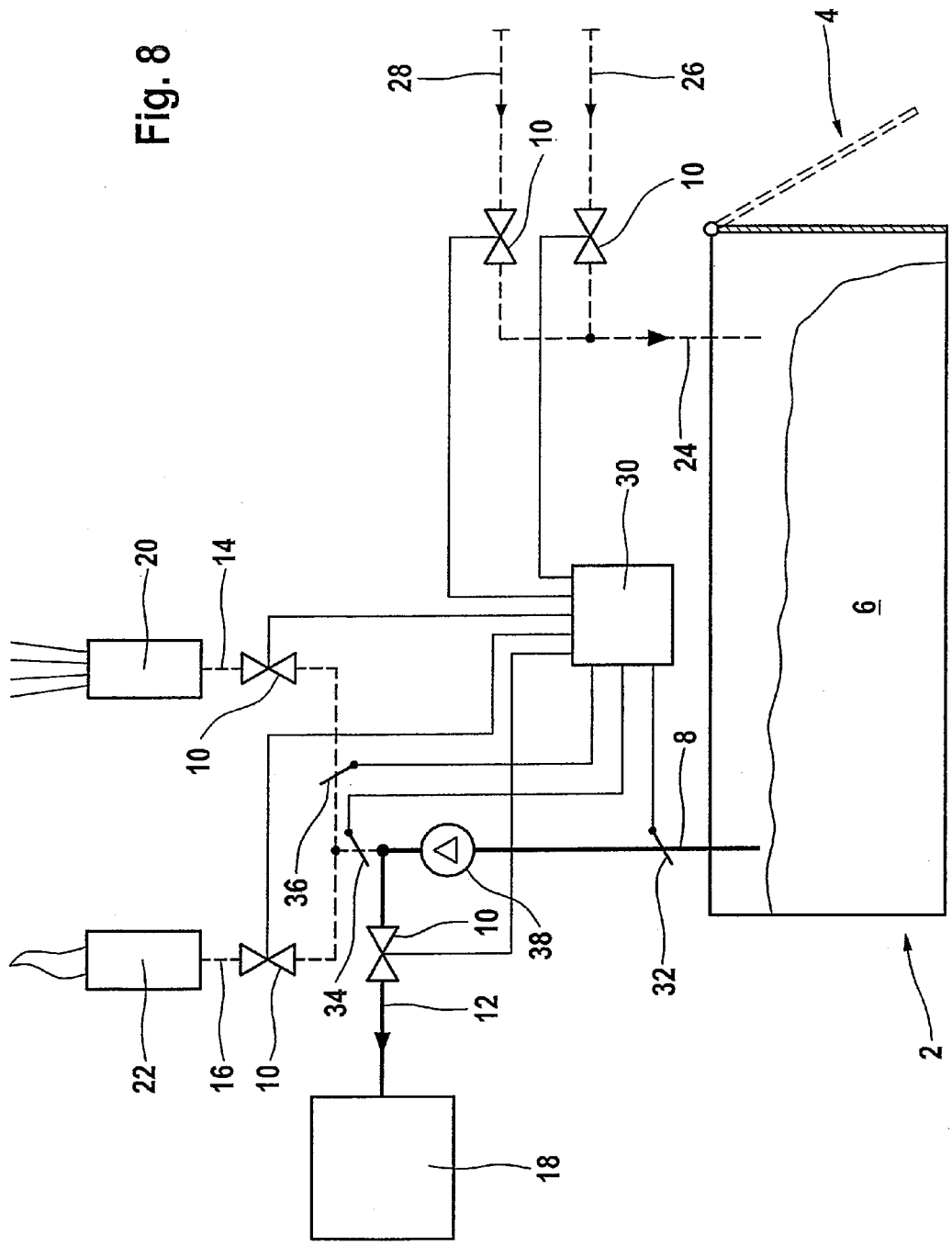
FIG. 8 shows a schematic illustration of a second embodiment of the invention with a fermenter.

In the embodiment described above, all the measurement sensors 32, 34, 36 are arranged in the biogas outlet 8. Alternatively, the second and third measurement sensors 24, 36 can also be arranged in the first and second biogas/off-gas lines 14, 16, respectively. FIG. 8 shows an alternative refinement of the invention, which differs from the embodiment shown in FIGS. 1 to 7, in that the first and second biogas/off-gas lines 14, 16 are combined to form a common biogas/off-gas line 40, before they open into the biogas outlet 8. The second measurement sensor for detection of the carbon-dioxide concentration is arranged in the common biogas/off-gas line 40, and the third measurement sensor 36 is arranged in the first biogas/off-gas line 14. Apart from this, the second embodiment of the invention corresponds to the first embodiment. The method of operation is also identical.

FIGS. 9 to 15 show a third embodiment of a biogas installation according to the present invention, in which three fermenters 2-1, 2-2 and 2-3 are provided, and are operated in parallel. Mutually corresponding components are provided with the same reference symbols. In the biogas installation shown in FIGS. 9 to 15, each of the three fermenters 2-i is provided with a purging gas inlet 24-1, 24-2 and 24-3, which can each be shut off by a valve 10. The three purging gas inlets 24-i are combined to form a common purging gas inlet 42. An off-gas line 26 and a fresh air line 28 open into the common purging gas inlet 42, and can each be shut off by a valve 10.

Each of the three fermenters 2-i is provided with a biogas outlet 8-1, 8-2 and 8-3, which can each be shut off by a valve 10. The first biogas/off-gas line 14 to the off-gas chimney 20 and the second biogas/off-gas line 16 to the off-gas flare 22 are combined to form a common biogas/off-gas line 40 in which a fan 38 is arranged. Downstream from the fan 38, the common biogas/off-gas line 40 splits into a first, a second and a third biogas/off-gas line element 40-1, 40-2 and 40-3. The first biogas/off-gas line element 40-1 opens between the valve 10 and the first biofermenter 2-1 into the first biogas outlet 8-1. The second biogas/off-gas line element 40-2 opens between the valve 10 and the second biofermenter 2-2 into the second biogas outlet 8-2. The third biogas/off-gas line element 40-3 opens between the valve 10 and the third biofermenter 2-3 into the third biogas outlet 8-3. The three biogas/off-gas line elements 40-1, 40-2 and 40-3 can each be shut off by a valve 10. The three biogas outlets 8-1, 8-2 and 8-3 open into a common biogas line 12, which leads to a cogeneration system or combined heat and power unit 18. An exhaust line 44 from the cogeneration system 18 opens into a second off-gas chimney 46. The off-gas line 26 is connected via a 3-way valve 48 to the exhaust line 44, that is to say the off-gas containing carbon dioxide which occurs in the cogeneration system 18 is used to purge a fermenter 2-i that is to be shut down. The 3-way valve allows the volume flow of the off-gas which is sent via the off-gas line 26 in order to purge a fermenter 2-i, and the amount of off-gas which is emitted via the second off-gas chimney 46 to the environment, to be regulated.

A first measurement sensor 32 is arranged in the common biogas line 12 in order to detect the methane concentration. A second measurement sensor 34 for detection of the carbon-dioxide concentration, a third measurement sensor 36 for detection of the volume flow, and a fourth measurement sensor 50 for detection of the methane concentration, are arranged in the common biogas/off-gas line 40, downstream from the fan 38 in the flow direction. The four measurement sensors 32, 34, 36 and 50 are connected to a control device 30. The various valves 10 are likewise connected to the control device. These control lines are not shown in FIGS. 9 to 15, for clarity reasons.

FIGS. 9 to 15 illustrate the processes for shutting down and restarting the second fermenter 2-2, with FIGS. 9 to 15 showing the same phases and operating states as FIGS. 1 to 7. The biogas production in the first and third fermenters 2-1 and 2-3 takes place continuously while the second fermenter 2-2 is being shut down and started again.

Figure 9:
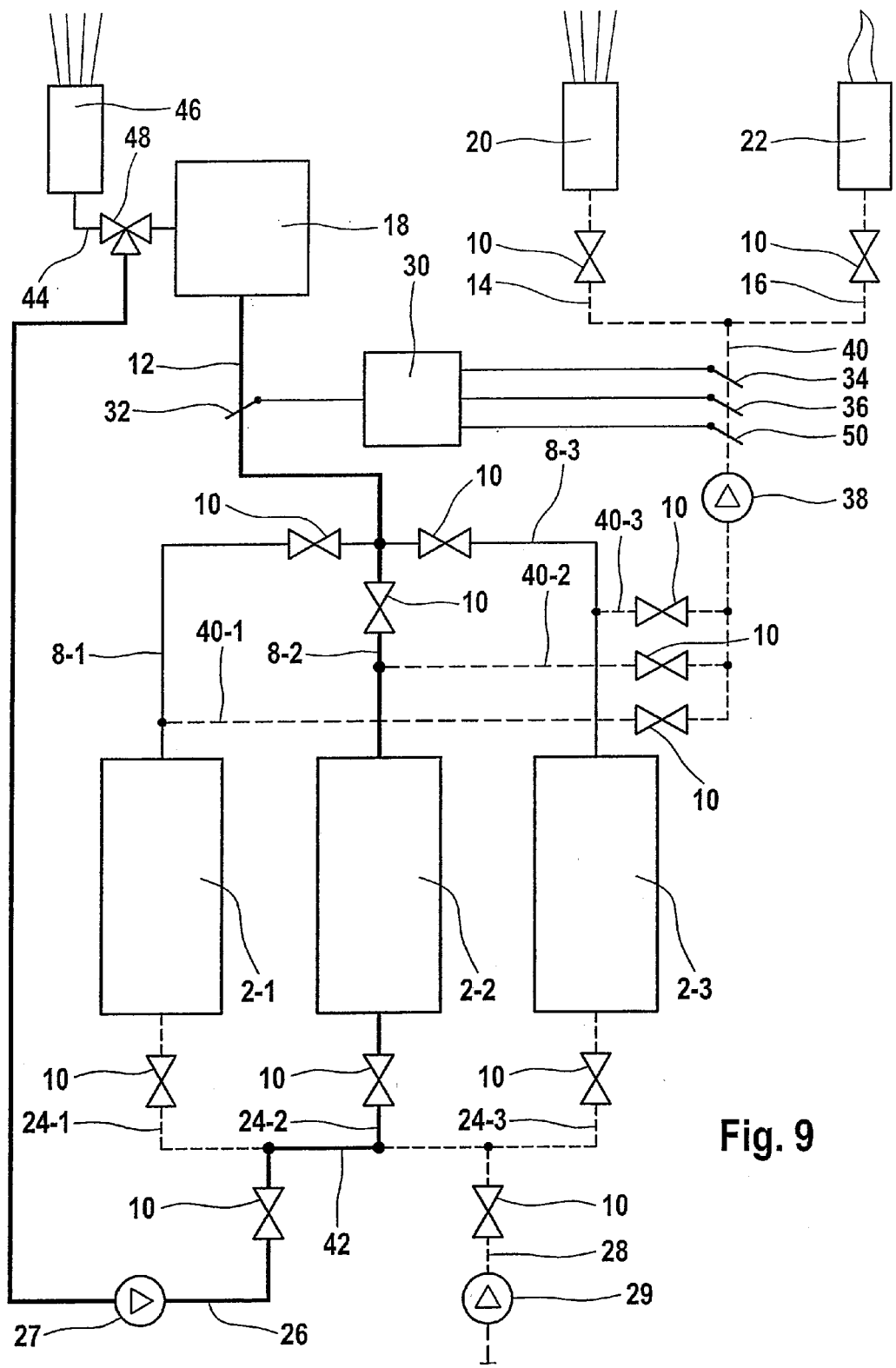
FIGS. 9 to 15 show schematic illustrations of various operating states of a biogas installation having three fermenters during the shut down process and while a fermenter is being (re)started.

FIG. 9 shows the first phase of shutting down the fermenter 2-2, in which off-gas containing carbon dioxide from the cogeneration system 18 is pumped via the 3-way valve 48 and the off-gas line 26, the off-gas fan 27 and the second purging gas inlet 24-2 into the interior of the fermenter 2-2. The second biogas outlet 8-2 is connected, as before, to the common biogas line 12, so that the biogas/off-gas mixture is supplied further to the cogeneration system 18.

Figure 10:
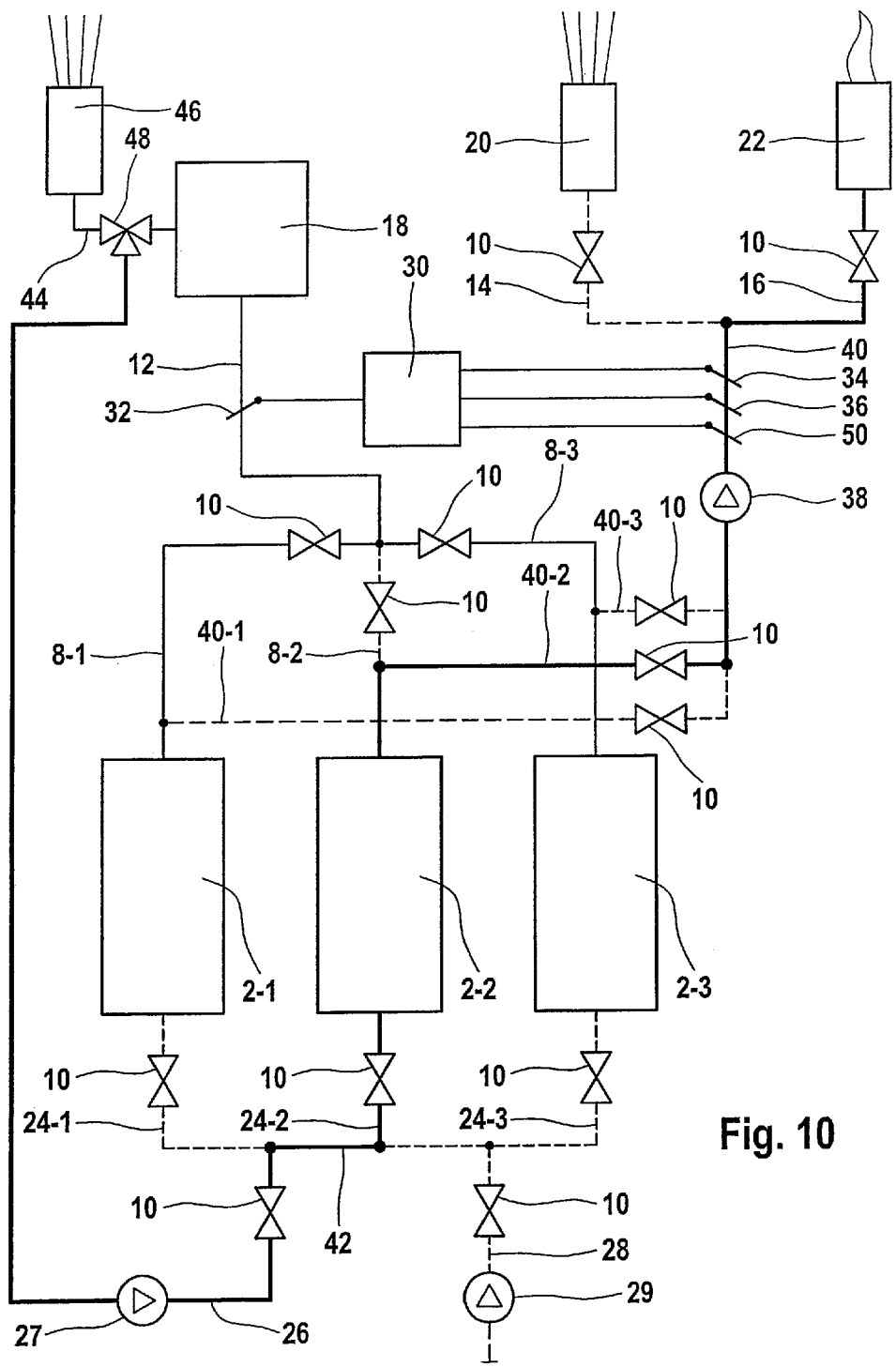

Only when the methane concentration detected by the first measurement sensor 32 in the common biogas line 12 has fallen below an upper limit value is the valve 10 in the second biogas outlet 8-2 closed by the control device 30, and the valve 10 in the second biogas/off-gas line element 40-2 and in the second biogas/off-gas line 16 is opened, as is illustrated in FIG. 10. In this second phase of shutting down the fermenter 2-2, the biogas/off-gas mixture is burnt in the off-gas flare 22. If necessary, this combustion process can be assisted by adding additional fuel.

Figure 11:
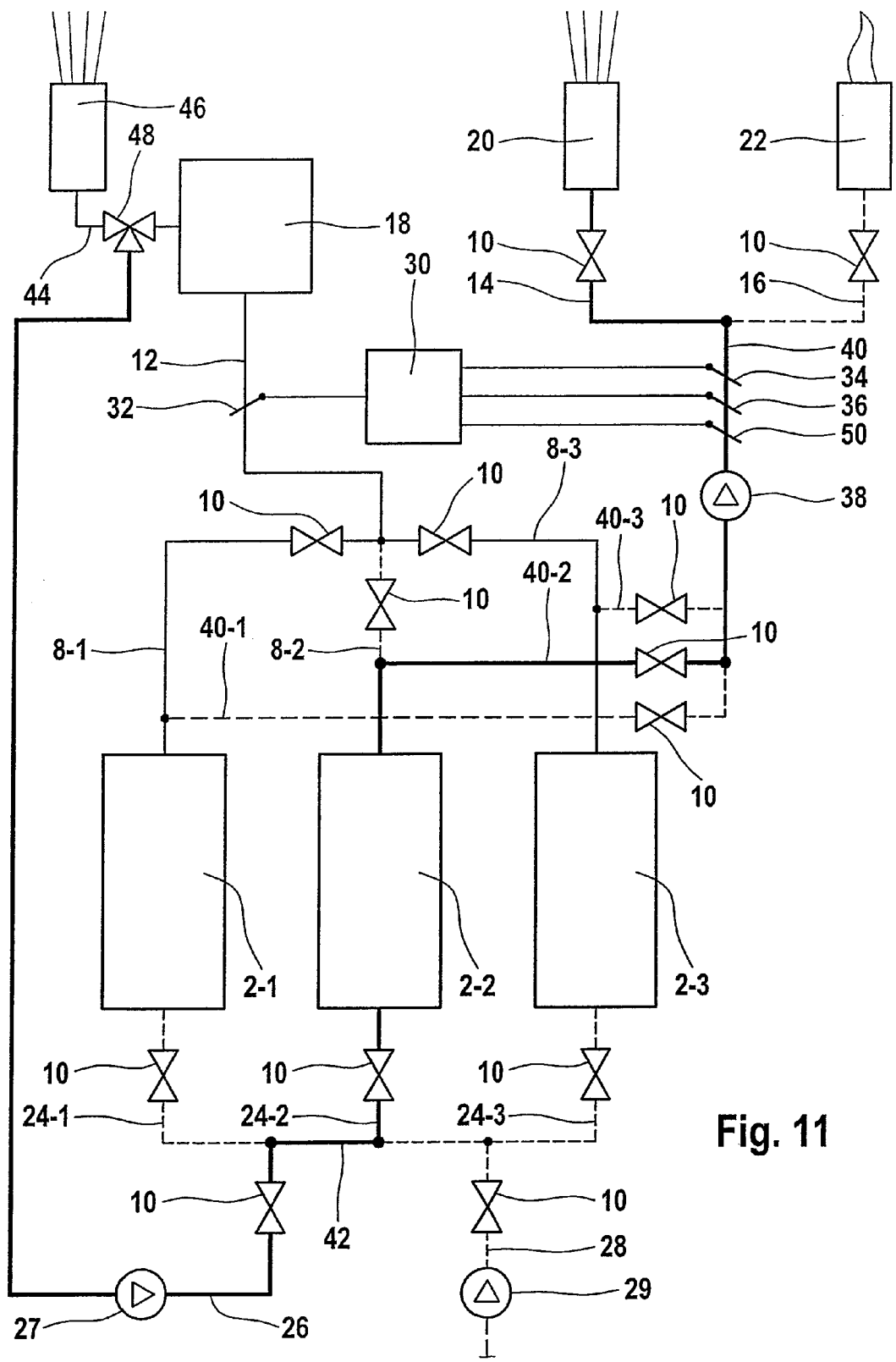

When the methane concentration detected by the fourth measurement sensor 50 in the common biogas/off-gas line 40 falls below a medium limit value, the valve 10 in the second biogas/off-gas line 16 is closed by the control device 30 and the valve 10 in the first biogas/off-gas line 14 is opened, as is illustrated in FIG. 11. In this third phase of shutting down the fermenter 2-2, the biogas/off-gas mixture is emitted to the environment via the off-gas chimney 20.

Figure 12:
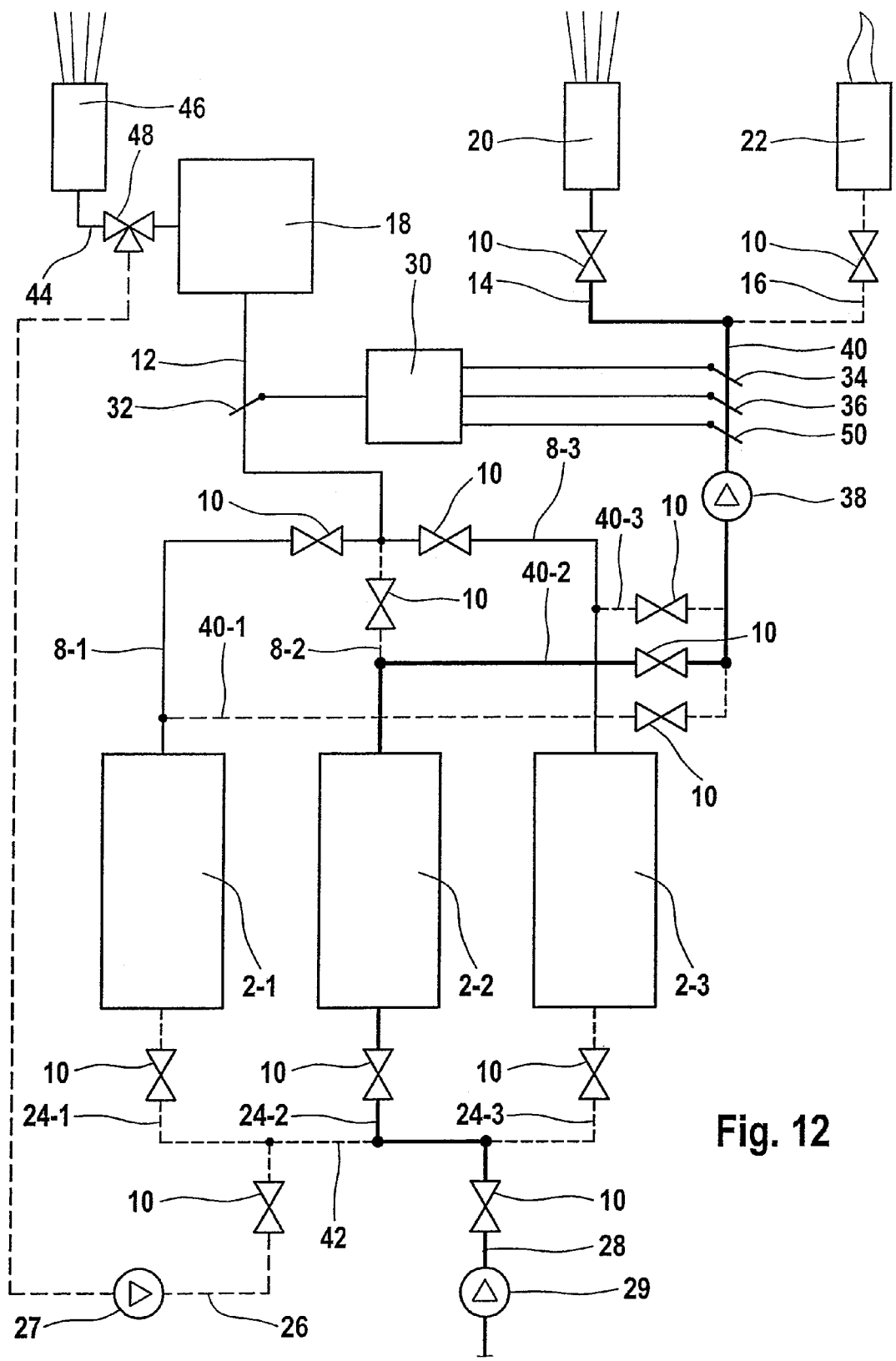

When the methane concentration detected by the fourth measurement sensor 50 in the common biogas/off-gas line 40 has fallen below a lower limit value, the valve 10 in the off-gas line 26 is closed by the control device 30, the 3-way valve 48 is switched appropriately, and the valve 10 in the fresh air line 28 is opened, as is illustrated in FIG. 12. In this fourth phase of shutting down the fermenter 2-2, the fresh air fan 29 pumps fresh air into the fermenter 2-2 via the fresh air line 28 and the purging gas inlet 24. The off-gas/air mixture is furthermore emitted to the environment via the second biogas outlet 8-2, the second biogas/off-gas line element 40-2, the common biogas/off-gas line 40 and the first biogas/off-gas line 14, in the off-gas chimney 20. If necessary, this can be assisted by the fan 38.

Figure 13:
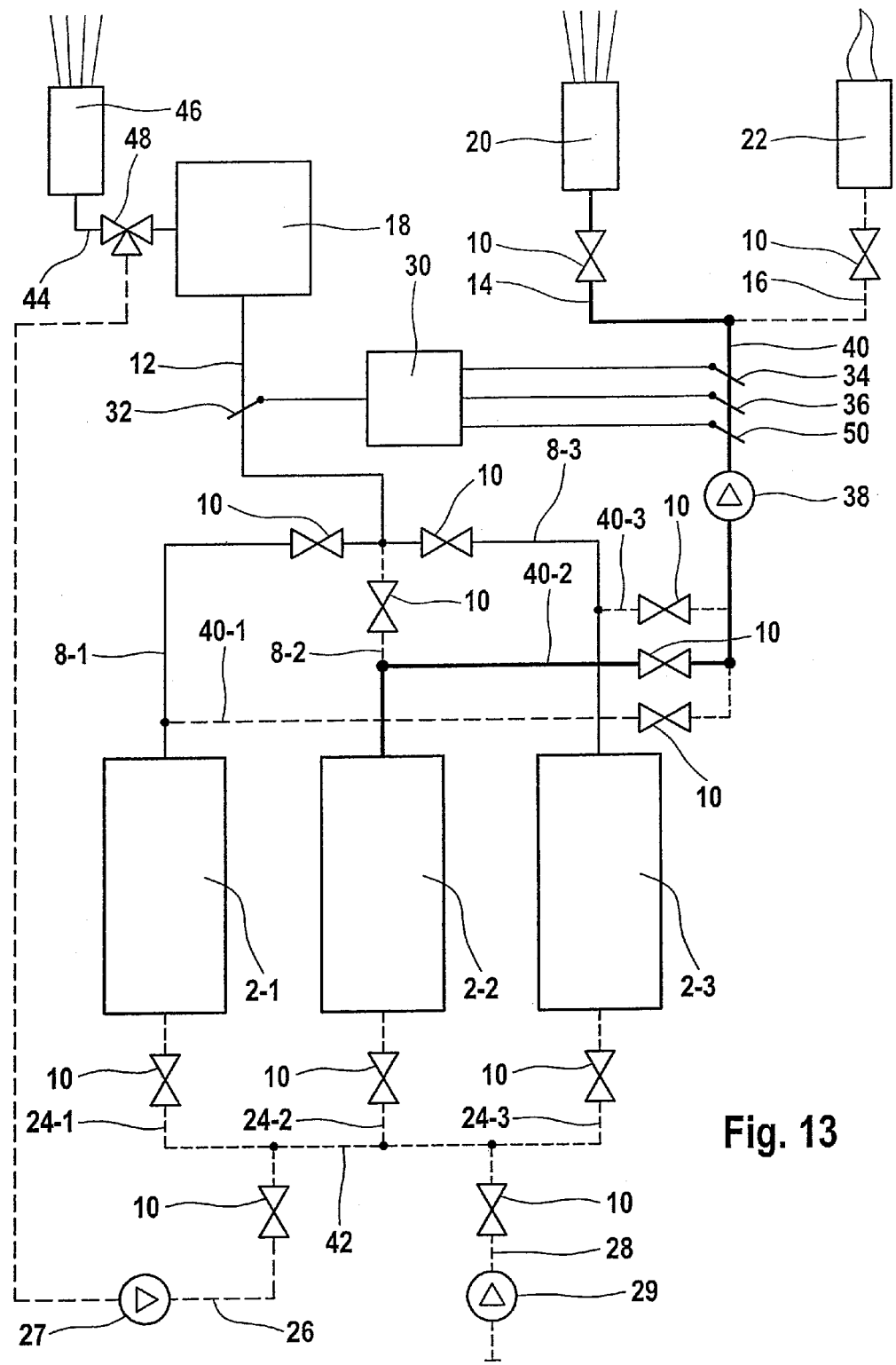

When the carbon-dioxide concentration detected by the second measurement sensor 34 in the common biogas line 40 has fallen below a first limit value, the valve 10 in the fresh air line 28 is closed by the control device 30, and the fresh air fan 29 is switched off, as is illustrated in FIG. 13. The loading and unloading opening, which is not illustrated in FIGS. 9 to 15, is opened. At the same time, fresh air is sucked in to the common biogas/off-gas line 40 via the fan 38 and via the open loading and unloading opening, and is emitted to the environment via the off-gas chimney 20.

This prevents any biogas residues which the fermented biomass still contains representing a risk to the operator during the unloading process. Exhaust gases from a tractor shovel which is used for loading and unloading are therefore also sucked out.

Figure 14:
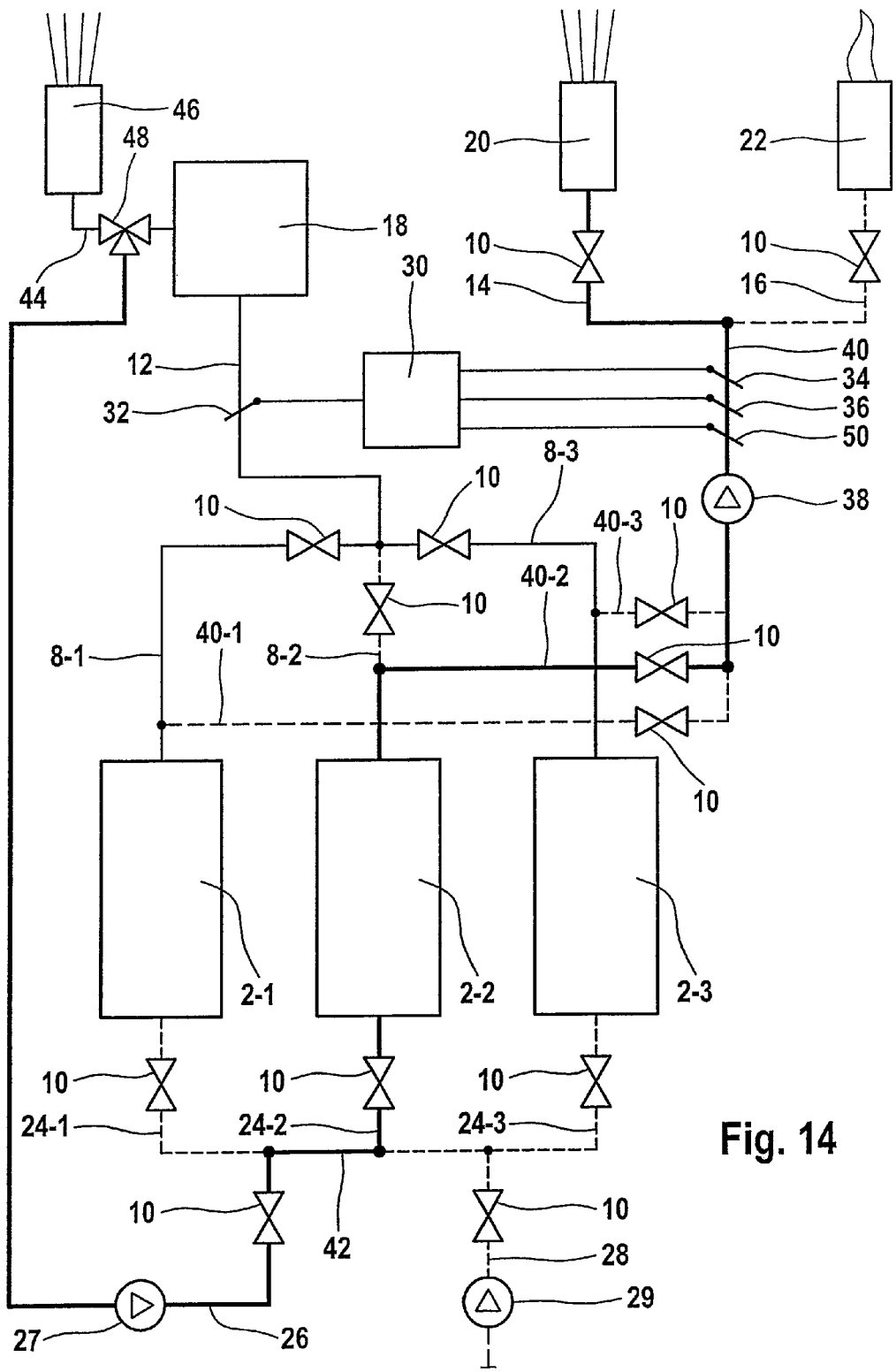

Once the fermenter 2-2 has been loaded with fresh biomass again, the loading and unloading opening is closed, the connection between the second biogas outlet 8-2 and the off-gas chimney 20 via the second biogas/off-gas line element 40-2, the common biogas/off-gas line 40 and the first biogas/off-gas line 14 is maintained, and the control device 30 opens the valve 10 in the off-gas line 26, and switches the 3-way valve 48 in the exhaust line 44 of the cogeneration system 18, so that off-gas containing carbon dioxide is pumped into the fermenter 2-2, see FIG. 14. This process continues until the carbon-dioxide concentration detected by the second measurement sensor 34 in the common biogas/off-gas line 40 reaches or exceeds a second limit value.

Figure 15:
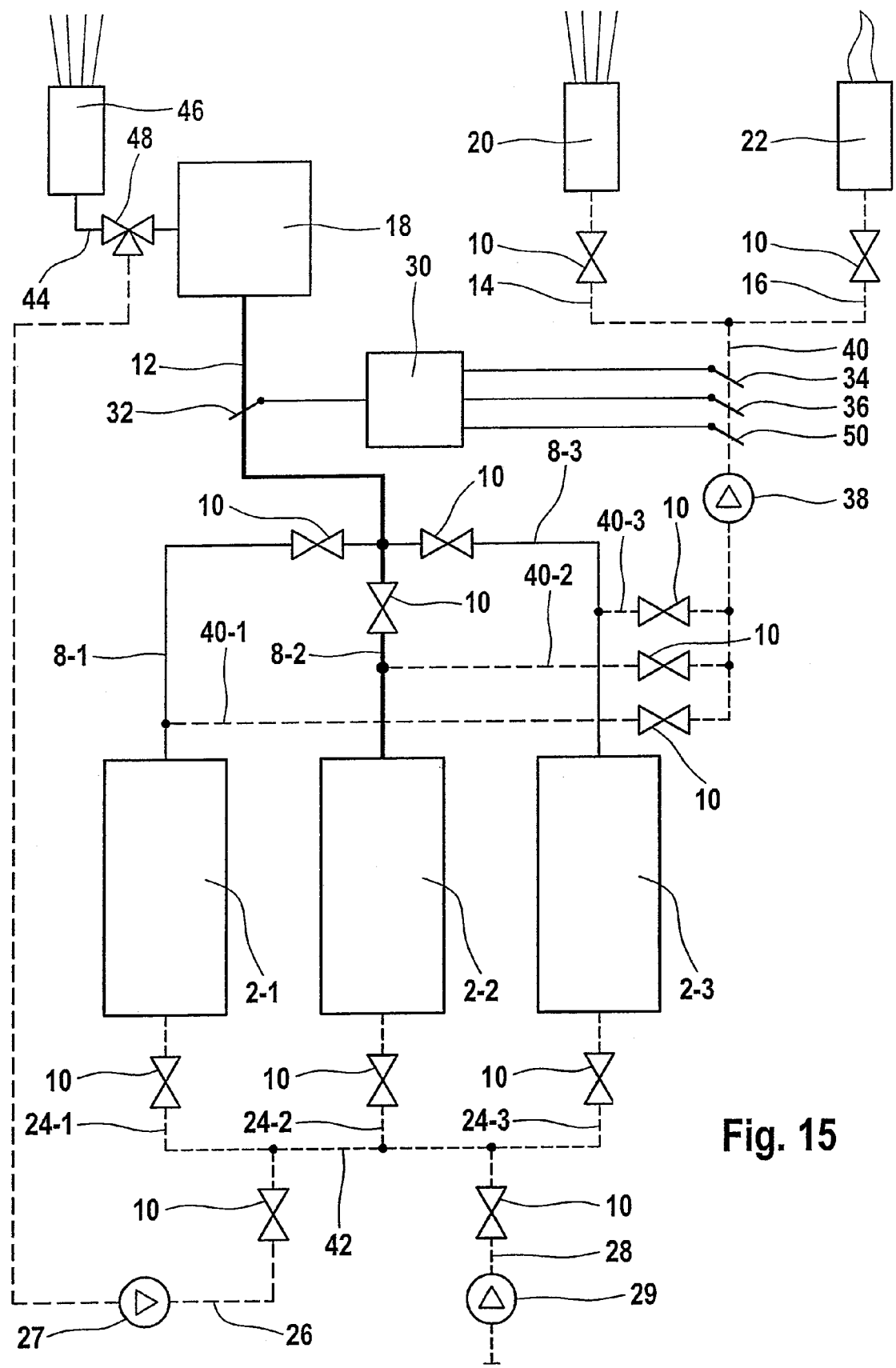

When this second limit value for the carbon-dioxide concentration has been reached, the control device 30 closes the valve 10 in the off-gas line 26, switches the 3-way valve 38, closes the valve 10 in the second biogas/off-gas line element 40-2 and opens the valve 10 in the second biogas outlet 8-2, as is illustrated in FIG. 15. This means that the second fermenter 2-2 has also once again reached the phase of biogas production, and the biogas produced in the fermenter 2-2 is supplied via the biogas line 12 to the cogeneration system 18. The biogas outlet 8-2 is not connected to the common biogas line 12 until the methane concentration detected by the fourth measurement sensor 50 has reached a fourth limit value. This fourth limit value matches the upper limit value.

The valve 10 in the off-gas line 26 may be omitted since its function can also be carried out by the 3-way valve 48.

Instead of directly connecting the biogas line 12 to the cogeneration system 18 it may be connected first to a gas processing device (not shown) to improve the gas quality. The biogas with improved quality is then fed to the congeneration system 18. Exhaust gas or off-gas from the gas processing device may be fed to the off-gas line 26.

The following text gives examples of numerical values of the various limit values:

Methane concentration: upper limit value 30% to 50%
medium limit value 10% to 20%
lower limit value 0% to 3%
fourth limit value 30% to 50%
Carbon-dioxide concentration: first limit value 0.5% to 2%
second limit value 5% to 15%

The off-gas volume flow in the off-gas line 26 is between 150 and 1000 m³/h, depending on the size of the fermenter and the amount of off-gas available. The fresh air volume flow in the fresh air line 28 is between 1000 and 5000 m³/h.

What is claimed is:

1. Method for shutting down a fermenter in a biogas installation, the biogas installation comprising the fermenter which operates on the principle of dry fermentation for production of biogas in the batch mode with a biogas outlet and a purging gas inlet; a biogas line connected to the biogas outlet, an off-gas line by means of which off-gas containing carbon dioxide is supplied to the purging gas inlet, an off-gas chimney connected to the biogas outlet via a first biogas/off-gas line, an off-gas flare connected via a second biogas/off-gas line to the biogas outlet, a fresh air line connected to the purging gas inlet, a control device for connection of the biogas outlet to the biogas line or to an off-gas chimney via the first biogas/off-gas line or to the off-gas flare via the second biogas/off-gas line and for connection of the purging gas inlet to the off-gas line or to the fresh air line, a measurement device which is connected to the control device and has a first measurement sensor for detection of the methane concentration and a second measurement sensor for detection of the carbon dioxide concentration in a gas mixture emerging from the at least one fermenter, and a loading and unloading opening, said method comprising the method steps of:

a) maintaining the connection between the biogas outlet and the biogas line;

b) connecting the off-gas line to the purging gas inlet of the fermenter to be shut down;

c) purging of the fermenter to be shut down with off-gas from the off-gas line until the methane concentration detected by the first measurement sensor has fallen to an upper limit value;

d) disconnecting the biogas line from the biogas outlet of the fermenter to be shut down;

e) connecting the biogas outlet of the fermenter to be shut down to the first biogas/off-gas line, and supply of the off-gas/biogas mixture to the off-gas chimney until the methane concentration detected by the first measurement sensor has fallen to a lower limit value, the lower limit value lower than the upper limit value;

f) disconnecting the off-gas line from the purging gas inlet of the fermenter to be shut down;

g) connecting the fresh air line to the purging gas inlet of the fermenter to be shut down, and supply of fresh air into the fermenter to be shut down, until the carbon-dioxide concentration detected by the second measurement sensor has fallen to a first limit value;

h) opening of the loading and unloading opening of the fermenter that has been shut down; and i) unloading the used biomass from the fermenter.

2. Method according to claim 1, characterised in that the following method steps are carried out between method step d) and method step e):

d1) connecting the biogas outlet of the fermenter to be shut down to the second biogas/off-gas line, and supplying the off-gas/biogas mixture to the off-gas flare until the methane concentration detected by the first measurement sensor has fallen to a medium limit value which is between the upper and the lower limit value; and d2) disconnecting the biogas outlet of the fermenter to be shut down from the second biogas/off-gas line.

3. Method according to claim 1, further comprising the method steps of:

j) connecting the fresh air line to the purging gas inlet and/or to the biogas outlet; and k) supplying fresh air into the fermenter that has been shut down via the loading and unloading opening by sucking out the gas mixture via the purging gas inlet and/or the biogas outlet while the fermenter that has been shut down is being unloaded and loaded.

4. Method according to claim 3, characterised in that, during method step k), the volume flow of the air/biogas/off-gas mixture sucked out via the purging gas inlet and/or the biogas outlet is monitored by the control device.

5. Method according to claim 1, characterised in that the off-gas line is connected to the exhaust pipe of an internal combustion engine.

6. Method according to claim 1, characterised in that the off-gas line is connected to the exhaust pipe of a biogas processing device which produces an off-gas containing carbon dioxide.

7. Method according to claim 1, characterised in that the off-gas line is connected to the exhaust of a fuel cell.

8. Method for starting a fermenter in a biogas installation, the biogas installation comprising the fermenter which operates on the principle of dry fermentation for production of biogas in the batch mode with a biogas outlet and a purging gas inlet; a biogas line connected to the biogas outlet, an off-gas line by means of which off-gas containing carbon dioxide is supplied to the purging gas inlet, an off-gas chimney connected to the biogas outlet via a first biogas/off-gas line, an off-gas flare connected via a second biogas/off-gas line to the biogas outlet, a fresh air line connected to the purging gas inlet, a control device for connection of the biogas outlet to the biogas line or to an off-gas chimney via the first biogas/off-gas line or to the off-gas flare via the second biogas/off-gas line and for connection of the purging gas inlet to the off-gas line or to the fresh air line, a measurement device which is connected to the control device and has a first measurement sensor for detection of the methane concentration and a second measurement sensor for detection of the carbon dioxide concentration in a gas mixture emerging from the at least one fermenter, and a loading and unloading opening, said method, comprising the steps of:

a) loading the fermenter with fresh biomass
b) closing of a loading and unloading opening;
c) connecting the biogas outlet to the first biogas/off-gas line;
d) connecting the off-gas line to the purging gas inlet of the fermenter to be started and supply of off-gas to the fermenter to be started until the carbon-dioxide concentration detected by the second measurement sensor reaches a second limit value which is higher than the first limit value;
e) disconnecting the off-gas line from the purging gas inlet;
f) disconnecting the first biogas/off-gas line from the biogas outlet; and
g) connecting the biogas line to the biogas outlet.

9. Method according to claim 8, characterised in that method step g) is carried out when the methane concentration detected by the first measurement sensor exceeds a cogeneration limit value which is equal to or higher than the upper limit.

10. Method according to claim 9, characterised in that the cogeneration limit value of the methane concentration is equal to the upper limit value of the methane concentration.

* * * * *